(12) United States Patent
Krier et al.

(10) Patent No.: US 10,575,881 B2
(45) Date of Patent: Mar. 3, 2020

(54) SELF-LOCKING SCREWDRIVER

(71) Applicant: CLARIANCE, Beaurains (FR)

(72) Inventors: Brice Krier, Dainville (FR); Yannick Pontois, Lievins (FR)

(73) Assignee: CLARIANCE, Beaurains (FR)

( * ) Notice: Subject to any disclaimer, the term of this patent is extended or adjusted under 35 U.S.C. 154(b) by 406 days.

(21) Appl. No.: 15/592,863

(22) Filed: May 11, 2017

(65) Prior Publication Data
US 2017/0333093 A1 Nov. 23, 2017

Related U.S. Application Data

(60) Provisional application No. 62/338,237, filed on May 18, 2016.

(51) Int. Cl.
*A61B 17/58* (2006.01)
*A61B 17/70* (2006.01)
*A61B 90/00* (2016.01)

(52) U.S. Cl.
CPC .... *A61B 17/7082* (2013.01); *A61B 2090/035* (2016.02)

(58) Field of Classification Search
CPC ............ A61B 17/8875; A61B 17/0401; A61B 17/1782; A61B 17/70176; A61B 17/7077; A61B 17/7079; A61B 17/708; A61B 17/7091; A61B 2017/0409; A61B 2017/0411; B25B 15/001; B25B 15/004–008; B25B 15/02; B25G 1/04; B25G 1/10
USPC .......... 81/58.1, 436, 451, 461; 606/300–321, 606/104, 279
See application file for complete search history.

(56) References Cited

U.S. PATENT DOCUMENTS

| 8,784,431 B1* | 7/2014 | Harder | A61B 17/7082 606/104 |
|---|---|---|---|
| 2009/0005787 A1* | 1/2009 | Crall | A61B 17/7037 606/104 |
| 2009/0275954 A1* | 11/2009 | Phan | A61B 17/7064 606/104 |
| 2015/0150605 A1* | 6/2015 | Saidha | A61B 17/7032 606/104 |
| 2016/0000478 A1 | 1/2016 | Fischer et al. | |

FOREIGN PATENT DOCUMENTS

| EP | 2 962 651 A1 | 1/2016 | |
|---|---|---|---|
| KR | 100930369 B1 * | 12/2009 | ......... A61B 17/7082 |
| WO | WO-2012057386 A1 * | 5/2012 | ......... A61B 17/7082 |
| WO | WO-2017198553 A1 * | 11/2017 | ........... A61B 17/708 |

* cited by examiner

*Primary Examiner* — Jessica Weiss
(74) *Attorney, Agent, or Firm* — Young & Thompson

(57) ABSTRACT

The self-locking screwdriver includes a guide tube inside which a clamping rod is guided and rotatably driven, one end of which is provided with a cavity which allows the rotational drive and tightening of an anchoring screw, ensuring the immobilization of an orthopedic implant against an osseous body of an individual, the screwdriver including, on the one hand, between The guide tube and the clamping rod, a blocking system cooperating with the guide tube in order to prevent the latter from being loosened from the orthopedic implant when the anchoring screw is tightened and, on the other hand, on the outer periphery of the guide tube, a gripping wheel for locking and/or unlocking the blocking system and the rotational drive of the guide tube.

13 Claims, 6 Drawing Sheets

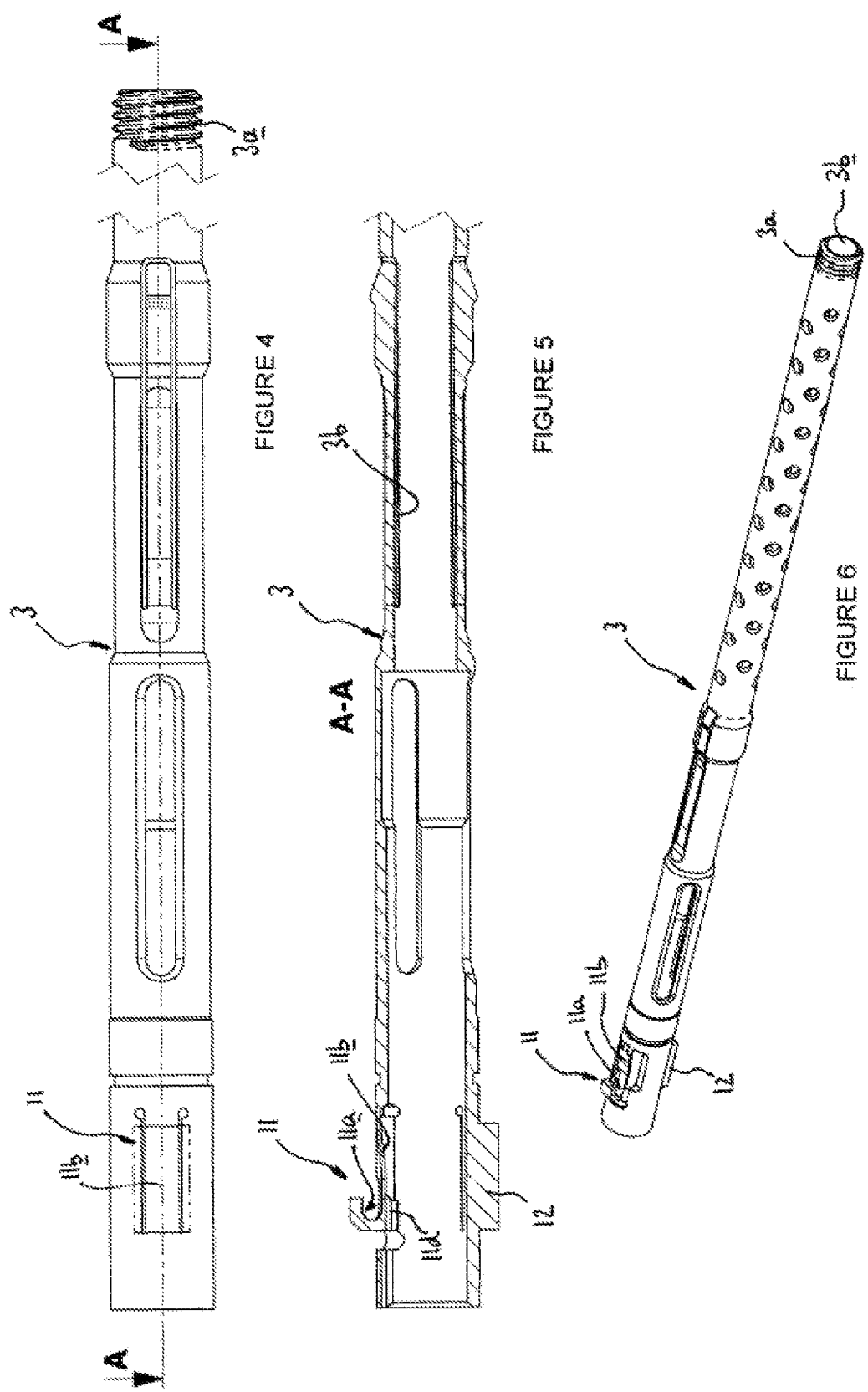

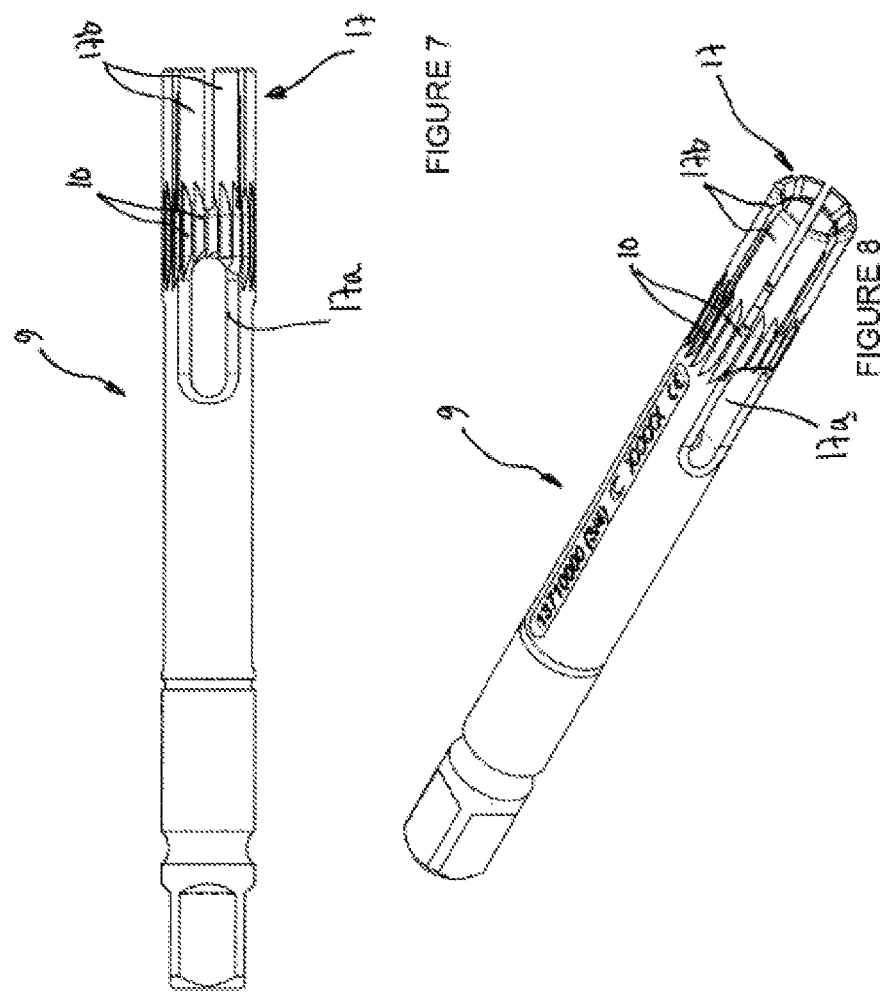

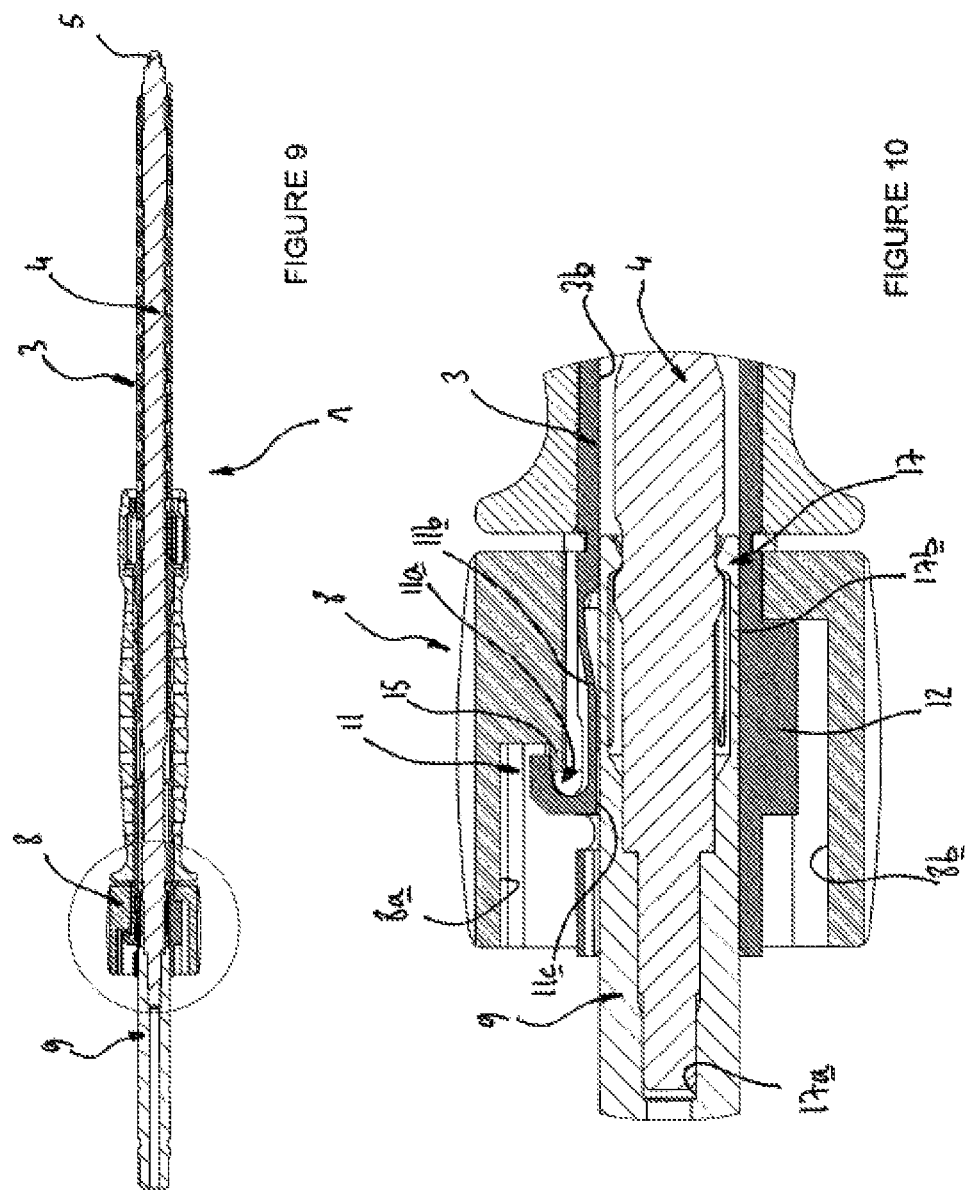

SELF-LOCKING SCREWDRIVER

FIELD OF THE INVENTION

The present invention relates to a self-locking screwdriver for placing, tightening and/or loosening orthopedic implants that are anchored in the tissues of a person's osseous body.

BACKGROUND OF THE INVENTION

Removable screwdrivers for anchoring bone screws for the retention of an orthopedic implant against an osseous body, and more particularly for attaching a connector for a spinal implant, are known from European Patent EP2962651.

The removable screwdriver includes a coupling portion for driving a rod whose distal end portion cooperates with the head of the pedicle screw, while said coupling portion is screwed into the tulip shape of the connector for spinal implant.

This type of screwdriver must, on the one hand, hold the connector firm and, on the other hand, allow the rotational drive of the anchoring screw for its fixation in the osseous tissues.

It must be noted that this type of screwdriver, under the effect of an external resistor, can become detached from the connector to be fixed, thus causing poor guidance of the implant and weakening the clamping rod.

SUMMARY OF THE INVENTION

The aim of the screwdriver according to the present invention is to solve this problem by proposing a blocking system enabling said screwdriver to be temporarily locked onto the implant during the anchoring time of the fixing screw in the osseous tissues.

The self-locking screwdriver according to the present invention comprises a guide tube inside which a clamping rod is guided and rotationally driven, one end of which is provided with a cavity enabling the rotational drive and the tightening of an anchoring screw, ensuring the immobilization of an orthopedic implant against an osseous body of an individual, said screwdriver comprising, on the one hand, between the guide tube and the clamping rod a blocking system cooperating with said guide tube in order to prevent the latter from being loosened from the orthopedic implant when the anchoring screw is being tightened and, on the other hand, on the outer periphery of the guide tube, a gripping wheel which locks and/or unlocks the blocking system and the rotational drive of said guide tube.

The self-locking screwdriver according to the present invention comprises a blocking system consisting of a connecting rod comprising on its periphery a series of teeth cooperating according to the direction of rotation of said rod with a retractable stop arranged in the guide tube.

The self-locking screwdriver according to the present invention has a retractable stop whose C-shaped profile has an inclined profile inside its opening.

The self-locking screwdriver according to the present invention comprises a retractable stop in which is arranged a flexible blade provided with a tooth on its internal face directed inside said guide tube.

The self-locking screwdriver according to the present invention comprises a retractable stop whose tooth has an arcuate profile which is arranged in the extension of the circular profile of the internal bore of the guide tube.

The self-locking screwdriver according to the present invention comprises a connecting rod comprising, in the extension of the teeth, a connecting device consisting, on the one hand, of a blind internal bore and, on the other hand, of an elastically deformable lamella arrangement for receiving and blocking the clamping rod in translation and rotation.

The automatic locking screwdriver according to the present invention comprises a torque transmission stud opposite the retractable stop of the guide tube.

The self-locking screwdriver according to the present invention comprises a gripping wheel having a first space inside which the retractable stop cooperates, and a second space disposed opposite the first space and inside which is housed the torque transmission stud.

The self-locking screwdriver according to the present invention comprises, inside the first space of the gripping wheel, a cam whose external profile comes into contact with the inclined face of the opening of the retractable stop.

The self-locking screwdriver according to the present invention comprises a second space whose internal profile makes it possible to delimit, in the vicinity of the external bore of the guide tube, a first stop called "screwing stop" and, on the opposite side, a second stop called "unscrewing stop" on which the torque transmission stud is supported according to the rotational direction of the gripping wheel around the guide tube.

BRIEF DESCRIPTION OF THE DRAWINGS

The description which follows with reference to the accompanying drawings and given by way of non-limiting examples, will allow to better understand the invention, the characteristics which it presents, and the advantages that it is capable of providing:

FIGS. 4 to 6 are views showing the guide tube of the self-locking screwdriver according to the invention.

FIGS. 7 and 8 are views showing the connecting rod of the blocking means of the self-locking screwdriver according to the invention.

FIGS. 9 and 10 are views showing the retractable stop of the blocking means of the self-locking screwdriver according to the invention.

DETAILED DESCRIPTION OF THE INVENTION

Figure 1:
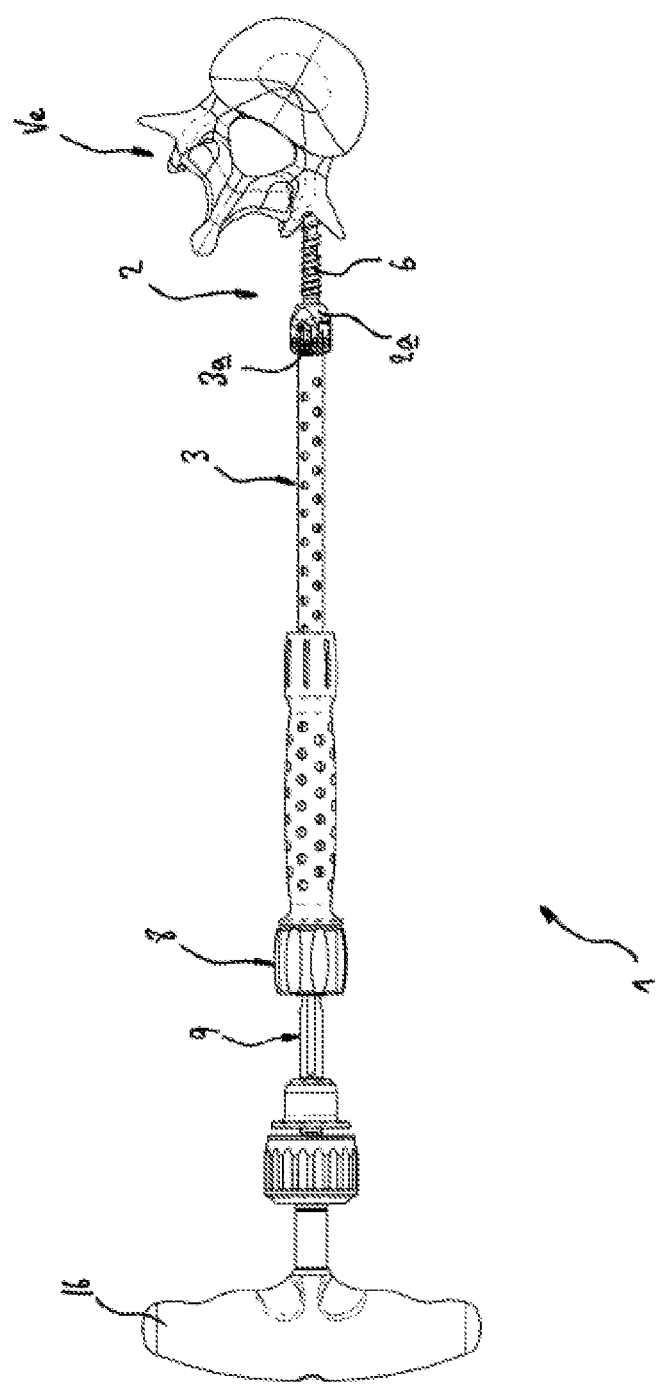
FIG. 1 is a perspective view showing a self-locking screwdriver for the placement and fixation of an orthopedic implant according to the invention.
Figure 2:
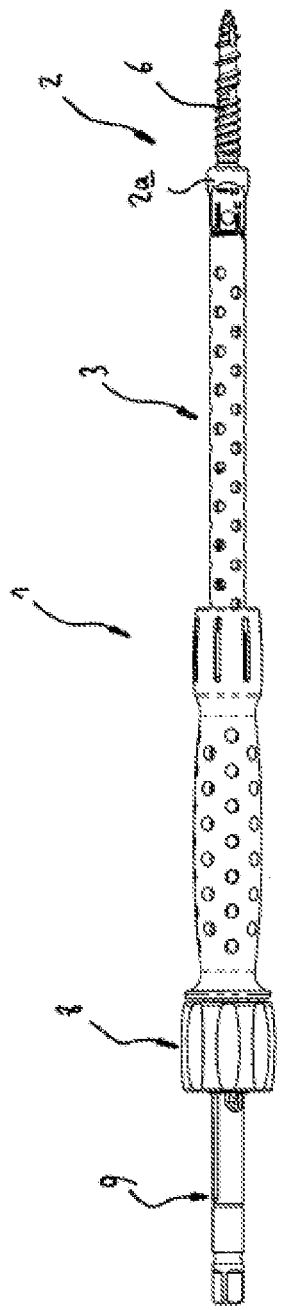
FIG. 2 is a profile view showing the self-locking screwdriver according to the invention.
Figure 3:
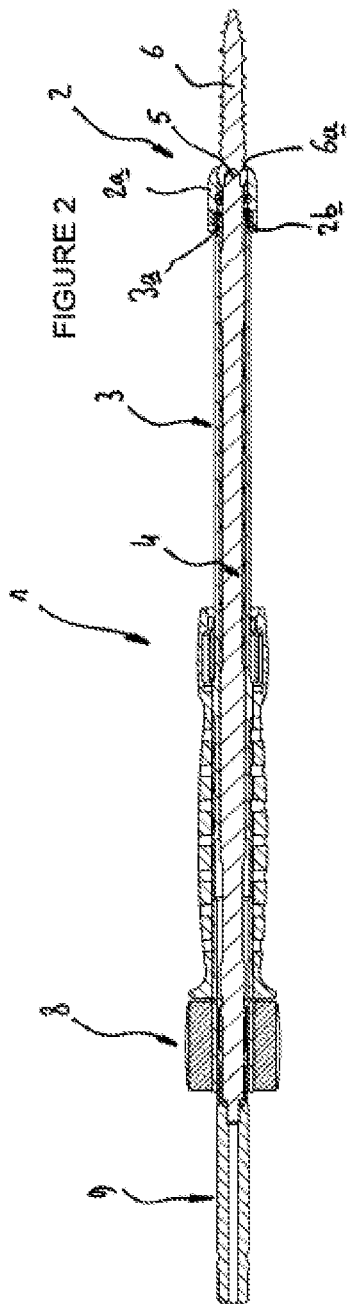
FIG. 3 is a sectional view showing the self-locking screwdriver according to the invention.

FIGS. 1 to 3 show a self-locking screwdriver 1 according to the present invention, comprising a guide tube 3 and a clamping rod 4 respectively cooperating with a U-shaped connector 2a and an anchoring screw 6 of an orthopedic implant 2.

The anchoring screw 6 is provided to pass through the connector 2a so that its head 6a with a spherical profile bears against the bottom of the U-shaped profile of the said connector 2a in order to ensure an angular and positioning freedom to the said connector with respect to the implantation axis said anchoring screw 6 in the body of a vertebra Ve.

The immobilization of the connector 2a in its definitive angular position about the axis of the anchoring screw 6 will take place when a connecting rod is placed in the bottom of the U-shaped profile of the said connector which will be blocked in translation and in rotation against the head 6a of the said screw 6 by means of a clamping screw, not illustrated, cooperating with a threaded zone 2b arranged in the upper and inner part of the U-shaped profile of the said connector.

Due to the freedom of movement between the connector 2a and the anchoring screw 6, the screwdriver 1 must necessarily come to rest in said connector while allowing the rotational drive of the anchoring screw 6.

The self-locking screwdriver 1 comprises a guide tube 3 provided at one of its ends with a threaded external profile 3a cooperating with the internal threaded zone 2b of the connector 2a so as to ensure the immobilization of said screwdriver 1 inside said connector 2a of the orthopedic implant 2.

At the opposite end of the threaded profile 3a, the guide tube 3 comprises, on its external periphery, a retractable stop 11 and, in a diametrically opposite direction, a transmission stud 12.

The retractable stop 11 has a C-shaped profile whose opening 11a is turned towards the threaded profile 3a. The retractable stop 11 is obtained by machining the external wall of the guide tube 3, delimiting a flexible blade 11b for ensuring a certain freedom of movement to said stop with respect to the longitudinal axis of said tube.

The flexible blade 11b of the retractable stop 11 comprises, on its internal face and directed inside the internal bore 3b of the guide tube 3, a tooth 11c whose arcuate profile is arranged in the extension of the circular profile of said internal bore.

The retractable stop 11 and the transmission stud 12 cooperate with a gripping wheel 8 arranged around the guide tube 3 and allowing, depending on its direction of rotation about said tube, to displace or not to displace said stop.

Figure 11:
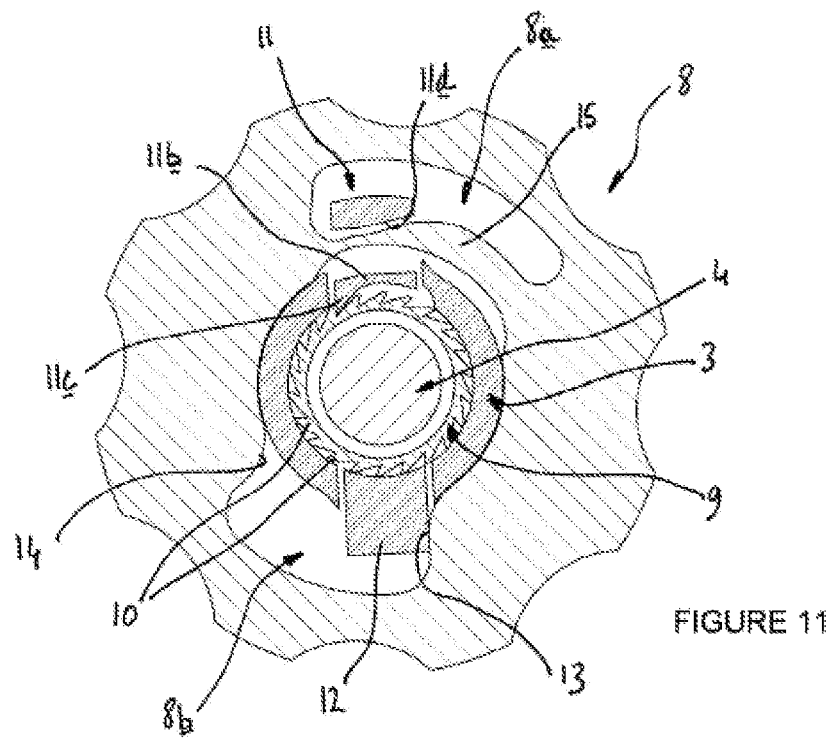
FIGS. 11 and 12 are cross-sectional views showing the locking and unlocking positions of the blocking means of the self-locking screwdriver according to the invention.
Figure 12:
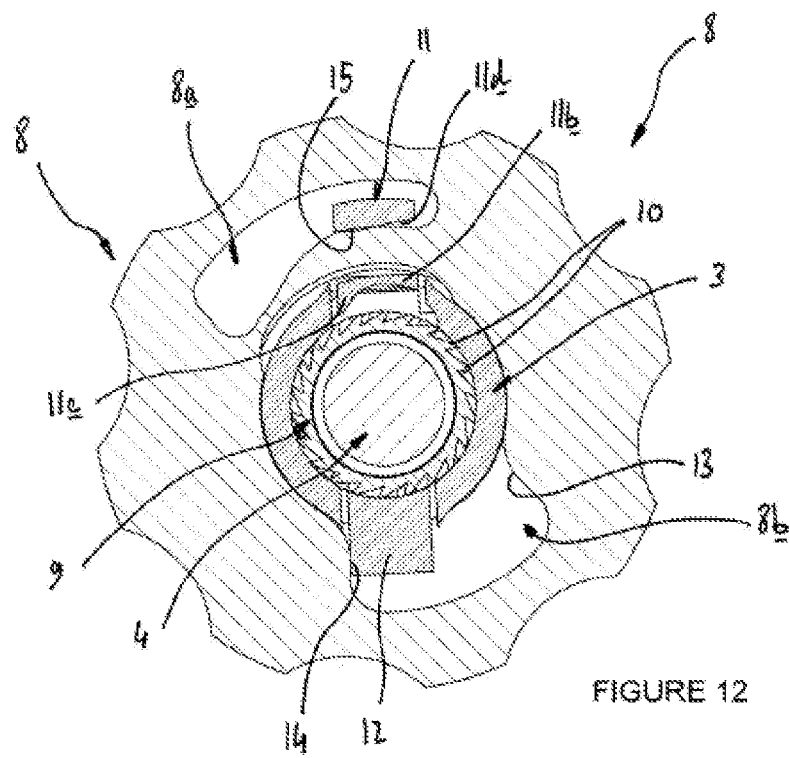

The gripping wheel 8 comprises a first space 8a inside which the C-shaped profile of the retractable stop cooperates. Inside the first space 8a is arranged a cam 15 whose external profile comes into contact with the inclined profile 11d of the opening 11a during the rotation of the gripping wheel 8 in order to move the tooth 11c away or closer from the retractable stop 11 of the central and longitudinal axis of the guide tube 3 (FIGS. 11 and 12).

The gripping wheel 8 has a second space 8b disposed opposite the first space 8a and inside which is housed the torque transmission stud 12, provided on the periphery of the guide tube 3.

The second space 8b has an internal profile for delimiting, in the vicinity of the external bore of the guide tube 3, a first stop 13 called the "screwing stop" and, on the opposite side, a second stop 14 called the "unscrewing stop", on which bears the stud 12 depending on the rotational direction of the gripping wheel 8 around said guide tube.

The self-locking screwdriver 1 comprises, between the guide tube 3 and the clamping rod 4, a connecting rod 9 for connecting the said clamping rod to a holding handle 16.

The connecting rod 9 comprises, at one of its ends and on its outer periphery, a series of teeth 10 whose external profile is complementary to that of the tooth 11c of the retractable stop 11.

The connecting rod 9 comprises, in the extension of the teeth 10, a connection device 17 consisting, on the one hand, of a blind internal bore 17a and, on the other hand, of an arrangement of elastically deformable blades 17b for receiving and blocking the clamping rod 4b in translation and rotation.

The clamping rod 4 comprises, opposite to its connection with the connecting rod 9, an external cavity 5 cooperating with the internal cavity formed in the head 6a of the anchoring screw 6 in order to allow the rotational drive of the latter when the guide tube 3 is immobilized on the connector 2a.

It will be understood from the above description that the placement of the orthopedic implant 2 in the vertebra Ve is carried out in the following manner:

The gripping handle 8 is driven in a clockwise rotation about the guide tube 3 in order to position the torque transmission stud 12 against the first stop 13, referred to as the "screwing stop", so that the torque is transmitted by the said stud 12 to the guide tube 3;

The profiles and angles respectively given to the teeth 10 of the connecting rod 9 and to the tooth 11c of the retractable stop 11 allow the tooth 11c, during the rotational drive of the guide tube 3, to skip the said teeth 10 of the connecting rod 9. There is therefore no obstacle in this rotational direction and the guide tube 3 can be screwed into the connector 2a of the implant 2;

When the guide tube 3 is completely immobilized in the connector 2a of the implant 2, the clamping rod 4 is rotated by means of the handle 16 and the connecting rod 9 in order to screw the anchoring screw 6 into the body of the vertebra Ve to fix the implant 2.

In the case of external friction caused, for example, by the neighboring flesh on the guide tube 3, causing an inverse force capable of unscrewing said guide tube 3 from the implant 2, it is noted that the latter is in fact maintained in counterclockwise rotation by a blocking system consisting of the tooth 11c of the retractable stop 11 which comes in opposition and in contact with the corresponding tooth 10 of the connecting rod 9, preventing said guide tube 3 from being unscrewed from the connector 2.

It is also understood from the description that the blocking device of the screwdriver 1 can be unlocked in order to enable the guide tube 3 to be unscrewed from the connector 2a of the implant 2 after its anchoring in the osseous body by means of the anchoring screw 6.

The unlocking of the blocking system is effected by a counter-clockwise movement of the gripping wheel 8 around the guide tube 3.

Indeed, a slack in the rotation between the gripping wheel 8 and the guide tube 3 allows releasing the tooth 11c from the retractable stop 11 which is lifted during the rotation by virtue of the cam shape 15 provided in the first space 8a of the gripping wheel 8.

The tooth 11c is thus released from the teeth 10 of the connecting rod 9.

Simultaneously with the counterclockwise rotation of the gripping wheel 8, the torque transmission stud 12 comes to rest against the second stop 14 called the "unscrewing stop", provided in the second space 8b of the said wheel.

The torque is then transmitted to the guide tube 3 which is unscrewed from the connector 2a of the implant 2.

It should be noted that the blocking system arranged to lock the guide tube 3 in counterclockwise rotation facilitates the use of the screwdriver 1 and the tightening of the anchoring screw 6 in the osseous body, especially when the latter is independent of the connector 2a of the implant 2.

It should moreover be understood that the foregoing description was given only by way of example and that it does not, in any way, limit the scope of the invention, and that replacing the details of execution described therein by any other equivalent would not fall outside the scope of the invention.

The invention claimed is:

1. A self-locking screwdriver, comprising: a guide tube; and a clamping rod, located inside the guide tube, a first end of the clamping rod provided with a cavity enabling a rotational drive and tightening of an anchoring screw for ensuring immobilization of an orthopedic implant against an osseous body of an individual, wherein a blocking system is provided between the guide tube and the clamping rod, the blocking system cooperating with the guide tube in such a manner as to prevent the guide tube from loosening from the orthopedic implant when the anchoring screw is being tightened, wherein a gripping wheel is provided on an outer periphery of the guide tube, the gripping wheel configured for locking and/or unlocking the blocking system and the rotational drive of said guide tube, wherein the blocking system includes a connecting rod that has, on a periphery thereof, a series of teeth that cooperate, as a function of a directional rotation of the rod, with a retractable stop arranged within the guide tube, and wherein the retractable stop comprises a flexible blade provided with a tooth located on an inner face of the flexible blade and directed inside said guide tube.

2. The self-locking screwdriver according to claim 1, wherein the retractable stop has a C-shaped profile.

3. The self-locking screwdriver according to claim 2, wherein the gripping wheel includes a first space therein, inside which the retractable stop cooperates, and a second space arranged opposite to the first space, inside which a torque transmission stud is housed.

4. The self-locking screwdriver according to claim 1, wherein the tooth has an arcuate portion which is arranged in an extension of a circular portion of an the internal bore of the guide tube.

5. The self-locking screwdriver according to claim 4, wherein the gripping wheel includes a first space therein, inside which the retractable stop cooperates, and a second space arranged opposite to the first space, inside which a torque transmission stud is housed.

6. The self-locking screwdriver according to claim 1, wherein the connecting rod further comprises a connection device comprising a blind internal bore and an elastically deformable blade arrangement for receiving and blocking the clamping rod in translation and in rotation.

7. The self-locking screwdriver according to claim 6, wherein the gripping wheel includes a first space therein, inside which the retractable stop cooperates, and a second space arranged opposite to the first space, inside which a torque transmission stud is housed.

8. The self-locking screwdriver according to claim 1, wherein the guide tube has a torque transmission stud opposite the retractable stop.

9. The self-locking screwdriver according to claim 8, wherein the gripping wheel includes a first space therein, inside which the retractable stop cooperates, and a second space arranged opposite to the first space, inside which a torque transmission stud is housed.

10. The self-locking screwdriver according to claim 1, wherein the gripping wheel includes a first space therein, inside which the retractable stop cooperates, and a second space arranged opposite to the first space, inside which a torque transmission stud is housed.

11. The self-locking screwdriver according to claim 10, wherein a cam is provided inside the first space, and wherein an external portion of the cam comes into contact with an inclined portion of the retractable stop.

12. The self-locking screwdriver according to claim 10, wherein the second space has an internal portion that allows delimiting, at an external bore of the guide tube, a first stop and, on an opposite side thereof, a second stop on which the torque transmission stud bears as a function of the directional rotation of the gripping wheel around said guide tube.

13. A self-locking screwdriver, comprising: a guide tube; and a clamping rod, located inside the guide tube, a first end of the clamping rod provided with a cavity enabling a rotational drive and tightening of an anchoring screw for ensuring immobilization of an orthopedic implant against an osseous body of an individual, wherein a blocking system is provided between the guide tube and the clamping rod, the blocking system cooperating with the guide tube in such a manner as to prevent the guide tube from loosening from the orthopedic implant when the anchoring screw is being tightened, wherein a gripping wheel is provided on an outer periphery of the guide tube, the gripping wheel configured for locking and/or unlocking the blocking system and the rotational drive of said guide tube, wherein the blocking system includes a connecting rod that has, on a periphery thereof, a series of teeth that cooperate, as a function of a directional rotation of the rod, with a retractable stop arranged within the guide tube, and wherein the connecting rod further comprises, adjacent the teeth, a connection device comprising a blind internal bore and an elastically deformable blade arrangement for receiving and blocking the clamping rod in translation and in rotation.

* * * * *